United States Patent

Moeller et al.

(10) Patent No.: US 6,371,993 B1
(45) Date of Patent: Apr. 16, 2002

(54) UTILIZATION OF ONIUM ALDEHYDES AND ONIUM KETONES FOR DYING FIBERS CONTAINING KERATIN

(75) Inventors: Hinrich Moeller, Monheim; Horst Hoeffkes, Duesseldorf, both of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/529,560

(22) PCT Filed: Oct. 5, 1998

(86) PCT No.: PCT/EP98/06308

§ 371 Date: Jun. 19, 2000

§ 102(e) Date: Jun. 19, 2000

(87) PCT Pub. No.: WO99/18916

PCT Pub. Date: Apr. 22, 1999

(30) Foreign Application Priority Data

Oct. 14, 1997 (DE) .......................................... 197 45 356

(51) Int. Cl.[7] .............................................. A61K 7/13
(52) U.S. Cl. ....................... 8/407; 8/405; 8/406; 8/407; 8/408; 8/409
(58) Field of Search ........................... 8/405, 406, 407, 8/408, 409

(56) References Cited

U.S. PATENT DOCUMENTS

| | | | |
|---|---|---|---|
| 4,865,774 A | 9/1989 | Fabry et al. | 252/551 |
| 4,931,218 A | 6/1990 | Schenker et al | 252/551 |
| 5,294,726 A | 3/1994 | Behler et al. | 554/98 |
| 5,378,244 A * | 1/1995 | Tamura et al. | 8/409 |
| 5,980,587 A | 11/1999 | Samain | 8/426 |
| 5,993,490 A | 11/1999 | Rondeau et al. | 8/409 |
| 6,001,135 A | 12/1999 | Rondeau et al. | 8/407 |

FOREIGN PATENT DOCUMENTS

| | | |
|---|---|---|
| DE | 38 23 354 | 1/1989 |
| DE | 37 25 030 | 2/1989 |
| DE | 39 26 344 | 2/1991 |
| DE | 195 27 121 | 1/1997 |
| FR | 2 757 384 | 6/1998 |
| FR | 2 757 388 | 6/1998 |
| WO | WO95/01772 | 1/1995 |
| WO | WO97/20545 | 6/1997 |

OTHER PUBLICATIONS

The Science of Hair Care, Chapter 7, pp. 235–261, published as vol. 7 of Dermatology, Marcel Dekker Inc., NY/Basle (1986).

The Science of Hair Care, Chapter 8, pp. 263–286 published as vol. 7 of Dermatology, Marcel Dekker Inc., NY/Basle (1986).

EU Inventory of Cosmetic Ingredients, Colipa, Mar. 1996—on diskette.

* cited by examiner

*Primary Examiner*—Yogendra N. Gupta
*Assistant Examiner*—Eisa Elhilo
(74) *Attorney, Agent, or Firm*—Wayne C. Jaeschke; Kimberly R. Hild; Daniel S. Ortiz

(57) ABSTRACT

The invention relates to the utilization of onium aldehydes and onium ketones of formula (1) or the derivatives thereof.

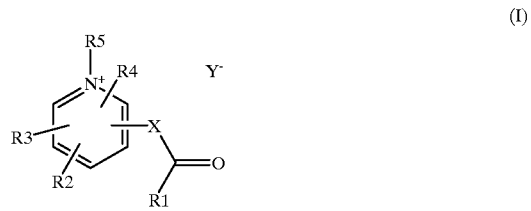

(I)

In the formula, $R^1$ represents a hydrogen atom, a $(C_1-C_4)$-alkyl group, an aryl group or a heteroaryl group. $R^2$, $R^3$, $R^4$, independent of one another, each represent a hydrogen atom, a halogen atom, a $(C_1-C_4)$-alkyl group, a $(C_1-C_4)$-alkoxyl group, hydroxy-$(C_1-C_4)$-alkoxyl group, hydroxyl group, nitro group, aryl group, trifluoromethyl group, amino group or $(C_1-C_4)$-acyl group. Said amino group can be substituted by $(C_1-C_4)$-alkyl groups. Two of the residuals can be combined to form a fused benzene ring. $R^5$ represents a $(C_1-C_4)$-alkyl group, aryl group, alkylaryl group or heteroaryl group. X designates a direct bonding or an optionally substituted vinyl group or phenyl group and Y— represents halogenide, benzenesulfonate, p-toluenesulfonate, methane sulfonate, trifluoromethane sulfonate, perchlorate, sulfate, hydrogen sulfate, tetrachlorozincate or N-oxide of the heterocyclic compound. In order to dye fibers containing keratin, onium aldehydes and onium ketones or the derivatives thereof are utilized in combination with at least one compound with a primary or secondary amino group or hydroxyl group. The compound is selected from primary or secondary aliphatic or aromatic amines, heterocyclic compounds containing nitrogen, amino acids, oligopeptides, said oligopeptides containing from 2 to 9 amino acids, as well as aromatic hydroxy compounds, and/or at least one CH-active compound.

23 Claims, No Drawings

UTILIZATION OF ONIUM ALDEHYDES AND ONIUM KETONES FOR DYING FIBERS CONTAINING KERATIN

FIELD OF THE INVENTION

This invention relates to the use of onium aldehydes and ketones and derivatives thereof for coloring keratin-containing fibers, more particularly human hair, to a composition containing onium aldehydes and ketones for coloring keratin-containing fibers and to a process for coloring keratin-containing fibers.

BACKGROUND OF THE INVENTION

In general, keratin-containing fibers, for example hair, wool or pelts, are dyed either with substantive dyes or with oxidation dyes which are formed by oxidative coupling of one or more primary intermediates with one another or with one or more secondary intermediates. Primary and secondary intermediates are also known as oxidation dye precursors.

The primary intermediates normally used are primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof.

Special representatives are, for example, p-phenylenediamine, p-toluylenediamine, 2,4,5,6-tetraaminopyrimidine, p-aminophenol, N,N-bis-(2-hydroxyethyl)-p-phenylenediamine, 2-(2,5-diaminophenyl)-ethanol, 2-(2,5-diaminophenoxy)-ethanol, 1-phenyl-3-carboxyamido-4-amino-5-pyrazolone, 4-amino-3-methylphenol, 2-aminomethyl-4-aminophenol, 2-hydroxy-4,5,6-triaminopyrimidine, 2,4-dihydroxy-5,6-diaminopyrimidine, 2,5,6-triamino-4-hydroxypyrimidine and 1,3-N,N'-bis-(2'-hydroxyethyl)-N,N'-bis-(4'-aminophenyl)-diaminopropan-2-ol.

The secondary intermediates used are generally m-phenylene-diamine derivatives, naphthols, resorcinol and resorcinol derivatives and m-aminophenol derivatives. Particularly suitable secondary intermediates are 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenol, 2-amino-3-hydroxy-pyridine, 2-methyl resorcinol, 5-methyl resorcinol and 2-methyl4-chloro-5-aminophenol.

With regard to the dyes suitable for use in the hair coloring and tinting formulations according to the invention, reference is also specifically made to Ch. Zviak's work The Science of Hair Care, Chapter 7 (pages 248–250; Substantive Dyes) and Chapter 8, pages 264–267; Oxidation Dye Precursors), published as Vol. 7 of the Series "Dermatology" (Editors: Ch. Culnan and H. Maibach), Marcel Dekker Inc., New York/Basel, 1986 and to the "Europäische Inventar der Kosmetik-Rohstoffe" published by the Europäische Gemeinschaft and available in diskette form from the Bundesverband Deutscher Industrie- und Handelsunternehmen für Arzneimittel, Reformwaren und Körperpflegemittel e.V., Mannheim, Germany.

Although intensive colors with good fastness properties can be obtained with oxidation dyes, the color is generally developed under the influence of oxidizing agents, such as $H_2O_2$ for example, which in some cases can result in damage to the fibers. In addition, some oxidation dye precursors or certain mixtures of oxidation dye precursors can occasionally have a sensitizing effect in people with sensitive skin. Although substantive dyes are applied under more moderate conditions, their disadvantage is that, in many cases, the colors obtained have inadequate fastness properties.

The problem addressed by the present invention was to provide colorants for keratin fibers, more especially human hair, which would be at least equivalent in quality to conventional oxidation hair dyes in regard to depth of color, grey coverage and fastness properties, but which would not necessarily have to contain oxidizing agents, such as $H_2O_2$ for example. Another problem addressed by the invention was to provide colorants with which a wide range of color tones could be obtained without any staining of the skin. In addition, the colorants according to the invention would have very little, if any, sensitizing potential.

It has now surprisingly been found that a combination of onium aldehydes and ketones as defined hereinafter and amines, hydroxy compounds and CH-active compounds are eminently suitable for coloring keratin-containing fibers. They give colors with excellent brilliance and depth of color and lead to a wide variety of color tones. The use of oxidizing agents is not necessary but, in principle, is not ruled out either.

Accordingly, the present invention relates to the use of onium aldehydes and ketones corresponding to formula I below or derivatives thereof:

BRIEF DESCRIPTION OF THE INVENTION

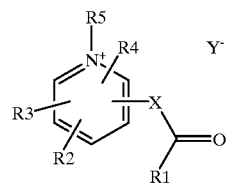

(I)

in which $R^1$ is a hydrogen atom, a $(C_{1-4})$ alkyl group, an aryl group or a heteroaryl group, $R^2$, $R^3$ and $R^4$ independently of one another represent a hydrogen atom, a halogen atom, a $(C_{1-4})$ alkyl group, a $(C_{1-4})$ alkoxy group hydroxy-$(C_{1-4})$-alkoxy group, hydroxy group, nitro group, aryl group, trifluoromethyl group, amino group which may be substituted by $(C_{1-4})$ alkyl groups or a $(C_{1-4})$ acyl group; two of the substituents together may also form a fused benzene ring, $R^5$ is a $(C_{1-4})$ alkyl group, aryl group, aralkyl group or heteroaryl group, X is a direct bond or a vinylene or phenylene group which may be substituted and $Y^-$ is halide, benzenesulfonate, p-toluene sulfonate, methane sulfonate, trifluoromethane sulfonate, perchlorate, sulfate, hydrogen sulfate or tetrachlorozincate or the N-oxide of the heterocycle, in combination with at least one compound containing a primary or secondary amino group or hydroxy group selected from primary or secondary aliphatic or aromatic amines, nitrogen-containing heterocyclic compounds, α- to ω-amino acids, oligopeptides made up of 2 to 9 amino acids and aromatic hydroxy compounds and/or at least one CH-active compound, for coloring keratin-containing fibers.

The present invention also relates to a composition for coloring keratin-containing fibers, more particularly human hair, characterized in that it contains
(A) one or more onium aldehydes or ketones corresponding to formula I or derivatives thereof and
(B) at least one compound containing a primary or secondary amino group or hydroxy group selected from primary or secondary aliphatic or aromatic amines, nitrogen containing heterocyclic compounds, α- to ω-amino acids, oligopeptides made up of 2 to 9 amino acids and aromatic hydroxy compounds and/or at least one CH-active compound; the reaction product of components A and B may also be present.

DETAILED DESCRIPTION OF THE INVENTION

In the contexts of the invention, keratin-containing fibers are understood to include wool, pelts, feathers and, in particular, human hair. In principle, however, the colorants according to the invention may also be used to color other natural fibers such as, for example, cotton, jute, sisal, linen or silk, modified natural fibers such as, for example, regenerated cellulose, nitro, alkyl or hydroxyalkyl or acetyl cellulose and synthetic fibers such as, for example, polyamide, polyacrylonitrile, polyurethane and polyester fibers.

The scope of the present invention also encompasses the use of substances which are reaction products of the individual components with one another.

Examples of derivatives of the compounds corresponding to formula I are oximes, acetals, ketals or hydrazones.

Suitable compounds corresponding to formula I which may be used as component A are the benzenesulfonates, p-toluene sulfonates, methane sulfonates, trifluoromethane sulfonates, perchlorates, sulfates, chlorides, bromides, iodides and/or tetrachlorozincates of 4-formyl-1-methyl pyridinium, 3-formyl-1-methyl pyridinium, 2-formyl-1-methyl pyridinium, 4-formyl-1-ethyl pyridinium, 2-formyl-1-ethyl pyridinium, 4-formyl-1-benzyl pyridinium, 2-formyl-1-benzyl pyridinium, 4-formyl-1,2-dimethyl pyridinium, 4-formyl-1,3-dimethyl pyridinium, 4-formyl-1-methyl quinolinium, 2-formyl-1-methyl quinolinium, 4-(2-formylvinyl)-1-methyl quinolinium, 4-acetyl-1-methyl pyridinium, 2-acetyl-1-methyl pyridinium, 4-acetyl-1-quinolinium, 4-acetyl-1-methyl quinolinium and 4-(2-formylvinyl)-1-methyl pyridinium, 2,6-dichloro-4-formyl-1-methyl pyridinium, 2,6-diphenyl4-formyl-1-methyl pyridinium, 4-benzoyl-1-methyl pyridinium, 4-propionyl-1-methyl pyridinium, 2-oximomethyl-1-methyl pyridinium, 4-pyridine carboxaldehyde-N-oxide and N-methyl pyridoxal.

The compounds corresponding to formula I used in accordance with the invention are known from the literature and are commercially obtainable or may be prepared in known manner from the N-heterocyclic carbonyl compound and an alkylating agent. To prepare the compound, the N-heterocyclic carbonyl compound and an excess of alkylating agent are dissolved in toluene and the resulting solution is heated with stirring for several hours to 90–100° C. until the starting compound has disappeared. The alkylating agent may be used in a 10- to 20-fold excess over the N-heterocyclic carbonyl compound. During the reaction, the quaternary ammonium compound generally precipitates in resin-like form. On completion of the reaction, the resin is repeatedly extracted with hot toluene in order completely to remove the alkylating agent and dried. The end product is generally resin-like or occasionally crystalline.

Suitable compounds containing a primary or secondary amino group as component B are, for example, primary aromatic amines, such as N,N-dimethyl-, N,N-diethyl-, N-(2-hydroxyethyl)-N-ethyl-, N,N-bis-(2-hydroxyethyl)-, N-(2-methoxyethyl)-, 2,3-, 2,4-, 2,5-dichloro-p-phenylenediamine, 2-chloro-p-phenylenediamine, 2,5-dihydroxy-4-morpholinoaniline dihydrobromide, 2-, 3-, 4-aminophenol, 2-aminomethyl-4-aminophenol, 2-hydroxymethyl-4-aminophenol, o-, p-phenylenediamine, o-toluylenediamine, 2,5-diaminotoluene, -phenol, -phenethol, 4-amino-3-methylphenol, 2-(2,5-diaminophenyl)-ethanol, 2,4-diaminophenoxyethanol, 2-(2,5-diaminophenoxy)-ethanol, 4-methylamino-, 3-amino-4-(2'-hydroxyethyloxy)-, 3,4-methylenediamino-, 3,4-methylenedioxyaniline, 3-amino-2,4-dichloro-, 4-methylamino-, 2-methyl-5-amino-, 3-methyl-4-amino-, 2-methyl-5-(2-hydroxyethylamino)-, 6-methyl-3-amino-2-chloro-, 2-methyl-5-amino-4-chloro-, 3,4-methylenedioxy-, 5-(2-hydroxyethylamino)-4-methoxy-2-methyl-, 4-amino-2-hydroxymethylphenol, 1,3-diamino-2,4-dimethoxybenzene, 2-, 3-, 4-aminobenzoic acid, -phenylacetic acid, 2,3-, 2,4-, 2,5-, 3,4-, 3,5-diaminobenzoic acid, 4-, 5-aminosalicylic acid, 3-amino-4-hydroxy-, 4-amino-3-hydroxybenzoic acid, 2-, 3-, 4-aminobenzenesulfonic acid, 3-amino4-hydroxybenzenesulfonic acid, 4-amino-3-hydroxynaphthalene-1-sulfonic acid, 6-amino-7-hydroxynaphthalene-2-sulfonic acid, 7-amino4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, aromatic anilines and phenols containing another aromatic radical corresponding to formula II:

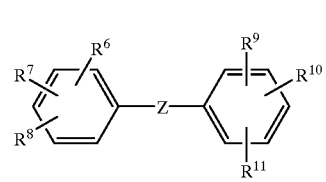

(II)

in which
R$^6$ is a hydroxy group or an amino group which may be substituted by C$_{1-4}$ alkyl, C$_{1-4}$ hydroxyalkyl or C$_{1-4}$ alkoxy-C$_{1-4}$-alkyl groups,
R$^7$, R$^8$, R$^9$, R$^{10}$ and R$^{11}$ represent hydrogen, a hydroxy group or an amino group which may be substituted by a C$_{1-4}$ alkyl, C$_{1-4}$ hydroxyalkyl, C$_{1-4}$ aminoalkyl or C$_{1-4}$ alkoxy-C$_{1-4}$-alkyl group or a carboxylic or sulfonic acid group and Z is a direct bond, a saturated or unsaturated optionally hydroxy-substituted carbon chain containing 1 to 4 carbon atoms, a carbonyl, sulfonyl or imino group, an oxygen or sulfur atom or a group corresponding to formula III:

(III)

in which
P is a direct bond, a CH$_2$ or CHOH group,
Q and Q' independently of one another represent an oxygen atom, an NR$^{12}$ group, where R$^{12}$ is hydrogen, a $C_{1-4}$ alkyl or a hydroxy-$C_{1-4}$-alkyl group, the group O—$(CH_2)_p$—NH or NH—$(CH_2)_{p'}$—O, where p and p'=2 or 3, and o is a number of 1 to 4, such as for example 4,4'-diaminostilbene, 4,4'-diaminostilbene-2,2'-disulfonic acid monosodium or disodium salt, 4-amino4'-dimethylaminostilbene, 4,4'-diaminodiphenyl -methane, -sulfide, -sulfoxide, -amine, 4,4'-diaminodiphenylamine-2-sulfonic acid, 4,4'-diaminobenzophenone, -diphenylether, 3,3',4,4'-tetraaminodiphenyl, 3,3'4,4'-tetraaminobenzophenone, 1,3-bis-(2,4-diaminophenoxy)-propane, 1,8-bis-(2,5-diaminophenoxy)-3,6-dioxaoctane, 1,3-bis-(4-aminophenylamino)-propane, -2-propanol, 1,3-bis-[N-(4-aminophenyl)-2-hydroxyethylamino]-2-propanol, N,N-bis-[2-(4-aminophenoxy)-ethyl]-methylamine, N-phenyl-1,4-phenylenediamine.

The compounds mentioned above may be used both in free form and in the form of their physiologically compatible salts, more especially as salts of inorganic acids, such as hydrochloric acid or sulfuric acid.

Suitable nitrogen-containing heterocyclic compounds are, for example, 2-, 3-, 4-amino-, 2-amino-3-hydroxy-, 2,6-diamino-, 2,5-diamino-, 2,3-diamino-, 2-dimethylamino-5-amino-, 2-methylamino-3-amino-6-methoxy-, 2,3-diamino-6-methoxy-, 2,6-dimethoxy-3,5-diamino-, 2,4,5-triamino-, 2,6-dihydroxy-3,4-dimethyl pyridine, 2,4-dihydroxy-5,6-diamino-, 4,5,6-triamino-, 4-hydroxy-2,5,6-triamino-, 2-hydroxy-4,5,6-triamino-, 2,4,5,6-tetraamino-, 2-methylamino-4,5,6-triamino-, 2,4-, 4,5-diamino-, 2-amino-4-methoxy-6-methyl pyrimidine, 3,5-diaminopyrazole, -1,2,4-triazole, 3-amino-, 3-amino-5-hydroxypyrazole, 2-, 3-, 8-aminoquinoline, 4-aminoquinaldine, 2-, 6-aminonicotinic acid, 5-aminoisoquinoline, 5-, 6-aminoindazole, 5-, 7-aminobenzimidazole, -benzothiazole, 2,5-dihydroxy-4-morpholinoaniline and indole and indoline derivatives and physiologically compatible salts thereof. Preferred examples of indole and indoline derivatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminindole. Also preferred are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxyindoline, 6-aminoindoline and 4-aminoindoline. The compounds mentioned above may be used both in free form and in the form of their physiologically compatible salts, for example as salts of inorganic acids, such as hydrochloric acid or sulfuric acid.

Suitable amino acids are any naturally occurring and synthetic amino acids, for example the amino acids obtainable by hydrolysis from vegetable or animal proteins, for example collagen, keratin, casein, elastin, soya protein, wheat gluten or almond protein. Both acidic and alkaline amino acids may be used. Preferred amino acids are arginine, histidine, tyrosine, phenyl alanine, DOPA (dihydroxyphenyl alanine), ornithine, lysine and tryptophane. However, other amino acids, such as 6-aminocaproic acid for example, may also be used.

The oligopeptides may be naturally occurring or synthetic oligopeptides and the oligopeptides present in polypeptide or protein hydrolyzates providing they are sufficiently soluble in water for use in the colorants according to the invention. Examples of such polypeptides are glutathione and the oligopeptides present in the hydrolyzates of collagen, keratin, casein, elastin, soya protein, wheat gluten or almond protein. These oligopeptides are preferably used together with compounds containing a primary or secondary amino group or with aromatic hydroxy compounds.

Suitable aromatic hydroxy compounds are, for example, 2-, 4-, 5-methyl resorcinol, 2,5-dimethyl resorcinol, resorcinol, 3-methoxyphenol, pyrocatechol, hydroquinone, pyrogallol, phloroglucinol, hydroxyhydroquinone, 2-, 3-, 4-methoxy-, 3-dimethylamino-, 2-(2-hydroxyethyl)-, 3,4-methylenedioxyphenol, 2,4-, 3,4-dihydroxybenzoic acid, -phenylacetic acid, gallic acid, 2,4,6-trihydroxybenzoic acid, -acetophenone, 2-, 4-chlororesorcinol, 1-naphthol, 1,5-, 2,3-, 2,7-dihydroxynaphthalene, 6-dimethylamino-4-hydroxy-2-naphthalene sulfonic acid, 3,6-dihydroxy-2,7-naphthalene sulfonic acid.

Examples of CH-active compounds are 1,2,3,3-tetramethyl-3H-indolium iodide, 1,2,3,3-tetraamethyl-3H-indolium-p-toluene sulfonate, 1,2,3,3-tetramethyl-3H-indolium methane sulfonate, Fischer's base (1,3,3-trimethyl-2-methyleneindoline) 2,3-dimethylbenzothiazolium iodide, 2,3-dimethylbenzothiazolium-p-toluene sulfonate, rhodanine, rhodanine-3-acetic acid, 1-ethyl-2-quinaldinium iodide, 1-methyl-2-quinaldinium iodide, barbituric acid, thiobarbituric acid, 1,3-dimethyl thiobarbituric acid, diethyl thiobarbituric acid, oxindole, 3-indoxyl acetate, coumaranone and 1-methyl-3-phenyl-2-pyrazolinone.

In all colorants, several different coloring substances may also be used together. Several different components from the groups of compounds containing a primary or secondary amino group, nitrogen-containing heterocycles, aromatic hydroxy compounds or amino acids may also be used together.

Oxidizing agents, for example $H_2O_2$, need not present where the onium aldehydes and ketones of formula I are used in accordance with the invention. However, it may be desirable in some cases to add hydrogen peroxide or other oxidizing agents to the compositions according to the invention to obtain shades which are lighter than the keratin-containing fibers to be colored. Oxidizing agents are generally used in a quantity of 0.01 to 6% by weight, based on the solution applied. A preferred oxidizing agent for human hair is $H_2O_2$.

The colorants according to the invention give a broad range of color tones in the range from yellow through yellow-brown, orange, brown-orange, mid-brown, dark brown, violet, dark violet to blue-black and black. Their fastness properties are excellent and their sensitizing potentials very low.

In one preferred embodiment, the colorants according to the invention contain typical substantive dyes, for example from the group of nitrophenylenediamines, nitroaminophenols, azo dyes, anthraquinones or indophenols, in addition to the compounds present in accordance with the invention in order further to modify the color tones. Preferred substantive dyes are the compounds known under the International names or commercial names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6- chloro4-nitrophenol, 4-ethylamino-3-nitrobenzoic acid and 2-chloro-6-ethylamino-1-hydroxy4-nitrobenzene. The compositions according to the invention in this embodiment contain the substantive dyes in a quantity of, preferably, 0.01 to 20% by weight, based on the colorant as a whole.

In addition, the compositions according to the invention may also contain naturally occurring dyes such as, for example, henna red, henna neutral, henna black, camomile blossom, sandalwood, black tea, black alder bark, sage, logwood, madder root, catechu, sedre and alkanet.

The oxidation dye precursors or the substantive dyes present, if any, do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

The colorants according to the invention produce intensive colors even at physiologically compatible temperatures of <45° C. Accordingly, they are particularly suitable for coloring human hair. For application to human hair, the colorants are normally incorporated in a water-containing cosmetic carrier. Suitable water-containing cosmetic carriers are, for example, creams, emulsions, gels or even surfactant-containing foaming solutions, for example shampoos or other formulations suitable for application to the keratin-containing fibers. If necessary, the colorants may even be incorporated in water-free carriers.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the compositions according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether, amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated C$_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example coconutalkyl dimethyl ammonium glycinate, N-acylaminopropyl-N,N-dimethyl ammonium glycinates, for example coconutacylaminopropyl dimethyl ammonium glycinate, and 2-alkyl-3-carboxymethyl-3-hydroxyethyl imidazolines containing 8 to 18 carbon atoms in the alkyl or acyl group and coconutacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a C$_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-coconutalkyl aminopropionate, coconutacyl aminoethyl aminopropionate and C$_{12-18}$ acyl sarcosine.

Nonionic surfactants contain, for example, a polyol group, a polyalkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer General Electric), SLM-55067 (manufacturer: Wacker) and Abil®-Quat 3270 and 3272 (manufacturer: Th. Goldschmidt; diquaternary polydimethyl siloxanes, quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamido-propyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, UV filters, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, imidazoles, tannins, pyrrole, opacifiers, such as latex, pearlizers, such as ethylene glycol mono- and distearate, propellants, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

It can be of advantage to the coloring result to add ammonium or metal salts to the colorants. Suitable metal salts are, for example, formates, carbonates, halides, sulfates, butyrates, valerates, caproates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminium, manganese, iron, cobalt, copper or zinc, sodium acetate, lithium bromide, calcium bromide, calcium gluconate, zinc chloride, zinc sulfate, magnesium chloride, magnesium sulfate, ammonium carbonate, chloride and acetate being preferred. These salts are preferably present in a quantity of 0.03 to 65 mmol and more preferably in a quantity of 1 to 40 mmol, based on 100 g of the colorant as a whole.

The pH value of the ready-to-use coloring compositions is normally in the range from 2 to 11 and preferably in the range from 5 to 9.

In order to color the keratin-containing fibers, more especially human hair, the colorants are generally applied to the hair in the form of the water-containing cosmetic carrier in a quantity of 100 g, left thereon for about 30 minutes and then rinsed out or washed out with a commercially available shampoo.

The compounds of components A and B may either be applied to the hair simultaneously or even successively, in which case it does not matter which of the two components is applied first. Reaction products of components A and B may also be used. The ammonium or metal salts optionally present may be added to the first component or to the second component. A time of up to 30 minutes can be allowed to pass between application of the first component and application of the second component. The fibers may even be pretreated with the salt solution.

Components A and B of the compositions according to the invention may be stored either separately or together either in the form of a liquid or paste-like preparation (aqueous or water-free) or as a dry powder. If the components are stored together in a liquid preparation, the preparation in question should be substantially free from water to reduce any risk of the components reacting. Where the reactive components are stored separately, they are mixed thoroughly together only shortly before application. Where the components are stored as a dry powder, a defined quantity of warm water (50 to 80° C.) is normally added and a homogeneous mixture prepared before application.

EXAMPLES

Preparation of Compounds Corresponding to Formula I 0.5 mol of the N-heterocyclic carbonyl compound and 1 mol of methyl sulfate as alkylating agent were dissolved in 500 ml of toluene and the resulting solution was heated with stirring for 5 hours to 100° C. The quaternary ammonium compound precipitates during the reaction. The reaction product was extracted twice with hot toluene in order completely to remove the alkylating agent and then dried. The end product was mostly resin-like or crystalline.

The following compounds were obtained:

4-acetyl-1-methyl pyridinium methane sulfonate, yellowish, resin-like 4-benzoyl-1-methyl pyridinium methane sulfonate: colorless, Mp. 178° C.

2- and 4-formyl-1-methyl quinolinium methane sulfonate: yellowish, resin-like 4-(2-formylvinylyl)-1-methyl pyridinium trifluoromethane sulfonate: yellowish, resin-like 4-acetyl-1-methyl quinolinium methane sulfonate: reddish, resin-like Preparation of a Coloring Solution A suspension of 10 mmol of a coloring component, 10 mmol of an amine, 10 mmol of sodium acetate and 1 drop of a 20% fatty alkyl ether sulfate solution in 100 ml of water was prepared. The suspension was briefly heated to around 80° C. and filtered after cooling, after which the pH value was adjusted to 6.

One tress of 90% grey, non-pretreated human hair was placed in this coloring solution for 30 minutes at 30° C. The colored tress was then rinsed for 30 seconds with luke-warm water, dried in a stream of warm air (30–40° C.) and then combed. The colors were visually evaluated in daylight.

The particular shades and depths of color are shown in the following Tables.

The depth of color was evaluated on the following scale: — very faint, if any, color (+) weak intensity + medium intensity +(+) medium to strong intensity ++ strong intensity ++(+) strong to very strong intensity +++ very strong intensity

TABLE 1

Coloring with 4-formyl-1-methylpyridinium benzenesulfonate

| Component B | Shade | Depth of color |
|---|---|---|
| — | — | — |
| 2,5-Diaminotoluene x $H_2SO_4$ | Orange-red | ++(+) |
| 2,4,5,6-Tetraaminopyrimidine x $H_2SO_4$ | Brown-orange | ++ |
| 1,8-bis-(2,5-diaminophenoxy)-3,6-dioxaoctane x 4 HCl | Orange brown | ++ |
| 2-Methylamino-3-amino-6-methoxy-pyridine x 2 HCl | Dark violet | +++ |
| 2-(2,5-Diaminophenyl)-ethanol x $H_2SO_4$ | Orange-red | ++(+) |
| 2-Aminomethyl-4-aminophenol x 2HCl | Yellow-olive brown | ++ |
| N,N-bis-(2-hydroxyethyl)-p-phenylene-diamine x HCl | Violet-red | ++(+) |
| 4,4'-Diaminodiphenylamine x $H_2SO_4$ | Black-violet | +++ |
| 2,6-Dimethoxy-3,5-diamino-pyridine x 2 HCl | Dark brown | +++ |
| Fischer's base | Violet-red | ++ |

TABLE 2

Coloring with 4-acetyl-1-methylpyridinium benzenesulfonate

| Component B | Shade | Depth of Color |
|---|---|---|
| — | — | — |
| 2,5-Diaminotoluene x $H_2SO_4$ | Red-brown | ++ |
| 2,4,5,6-Tetraaminopyrimidine x $H_2SO_4$ | Brown-red | ++ |
| 1,8-bis-(2,5-diaminophenoxy)-3,6-dioxaoctane x 4 HCl | Dark blue-grey | ++(+) |

TABLE 2-continued

Coloring with 4-acetyl-1-methylpyridinium benzenesulfonate

| Component B | Shade | Depth of Color |
|---|---|---|
| 2-Methylamino-3-amino-6-methoxy-pyridine × 2 HCl | Violet brown | +++ |
| 2,-(2,5-Diaminophenyl)-ethanol × H$_2$SO$_4$ | Red-rown | +(+) |
| 2-Aminomethyl-4-aminophenol × 2HCl | Yellow-brown | +(+) |
| N,N-bis-(2-hydroxyethyl)-p-phenylene-diamine × HCl | Violet-brown | ++ |
| 4,4'-Diaminodiphenylamine × H$_2$SO$_4$ | Black | +++ |
| 2,6-Dimethoxy-3,5-diamino-pyridine × 2 HCl | Black | +++ |

TABLE 3

Coloring with 4-benzoyl-1-methylpyridinium methanesulfonate

| Component B | Shade | Depth of color |
|---|---|---|
| — | — | — |
| 2,5-Diaminotoluene × H$_2$SO$_4$ | Dark violet | +++ |
| 2,4,5,6-Tetraaminopyrimidine × H$_2$SO$_4$ | Orange | ++ |
| 1,8-bis-(2,5-diaminophenoxy)-3,6-dioxaoctane × 4 HCl | Blue-black | +++ |
| 2-Methylamino-3-amino-6-methoxy-pyridine × 2 HCl | Black-brown | +++ |
| 2-(2,5-Diaminophenyl)-ethanol × H$_2$SO$_4$ | Red-rown | ++ |
| 2-Aminomethyl-4-aminophenol × 2HCl | Mid-brown | +(+) |
| N,N-bis-(2-hydroxyethyl)-p-phenylene-diamine × HCl | Violet-brown | ++ |
| 4,4'-Diaminodiphenylamine × H$_2$SO$_4$ | Black | +++ |
| 2,6-Dimethoxy-3,5-diamino-pyridine × 2 HCl | Black | +++ |

TABLE 4

Coloring with 2-oximomethyl-1-methylpyridinium methanesulfonate

| Component B | Shade | Depth of color |
|---|---|---|
| — | — | — |
| 2,5-Diaminotoluene × H$_2$SO$_4$ | Violet-brown | ++(+) |
| 2,4,5,6-Tetraaminopyrimidine × H$_2$SO$_4$ | Orange | ++(+) |
| 1,8-bis-(2,5-diaminophenoxy)-3,6-dioxaoctane × 4 HCl | Blue-black | +++ |
| 2-Methylamino-3-amino-6-methoxy-pyridine × 2 HCl | Dark brown | +++ |
| 2-(2,5-Diaminophenyl)-ethanol × H$_2$SO$_4$ | Violet-brown | ++ |
| 2-Aminomethyl-4-aminophenol × 2HCl | Light brown | + |
| N,N-bis-(2-hydroxyethyl)-p-phenylene-diamine × HCl | Mid-brown | ++ |
| 4,4'-Diaminodiphenylamine × H$_2$SO$_4$ | Blue-black | +++ |
| 2,6-Dimethoxy-3,5-diamino-pyridine × 2 HCl | Black | +++ |

TABLE 5

Coloring with 2-formyl-1-methylquinolinium trifluoromethanesulfonate

| Component B | Shade | Depth of color |
|---|---|---|
| — | Light brown | + |
| 2,5-Diaminotoluene × H$_2$SO$_4$ | Blue-black | +++ |
| 2,4,5,6-Tetraaminopyrimidine × H$_2$SO$_4$ | Violet-red | ++(+) |
| 1,8-bis-(2,5-diaminophenoxy)-3,6-dioxaoctane × 4 HCl | Blue-black | +++ |
| 2-Methylamino-3-amino-6-methoxy-pyridine × 2 HCl | Black | +++ |
| 2-(2,5-Diaminophenyl)-ethanol × H$_2$SO$_4$ | Violet-black | +++ |
| 2-Aminomethyl-4-aminophenol × 2HCl | Black | +++ |

TABLE 5-continued

Coloring with 2-formyl-1-methylquinolinium trifluoromethanesulfonate

| Component B | Shade | Depth of color |
|---|---|---|
| N,N-bis-(2-hydroxyethyl)-p-phenylene-diamine × HCl | Blue-black | +++ |
| 4,4'-Diaminodiphenylamine × H$_2$SO$_4$ | Blue-black | +++ |
| 2,6-Dimethoxy-3,5-diamino-pyridine × 2 HCl | Blue-black | +++ |
| 3-Methyl-4-aminophenol (oxyred) | Red | ++ |

TABLE 6

Coloring with 4-formyl-1-methylquinolinium methyl sulfate

| Component B | Shade | Depth of color |
|---|---|---|
| 2,5-Diaminotoluene × H$_2$SO$_4$ | Dark violet | +++ |
| 2-Methylamino-3-amino-6-methoxy-pyridine × 2 HCl | Dark blue | +++ |
| 2-(2,5-Diaminophenyl)-ethanol × H$_2$SO$_4$ | Dark violet | +++ |
| 2-Aminomethyl-4-aminophenol × 2HCl | Dark brown | ++ |
| N,N-bis-(2-hydroxyethyl)-p-phenylene-diamine × HCl | Dark blue | +++ |
| 2,6-Dimethoxy-3,5-diamino-pyridine × 2 HCl | Dark brown | +++ |

TABLE 7

Coloring with 4-formyl-1-methylquinolinium methanesulfonate

| Component B | Shade | Depth of color |
|---|---|---|
| — | Pink | + |
| 2,5-Diaminotoluene × H$_2$SO$_4$ | Brown-violet | +++ |
| 2,4,5,6-Tetraaminopyrimidine × H$_2$SO$_4$ | Dark violet-red | +++ |
| 1,8-bis-(2,5-diaminophenoxy)-3,6-dioxaoctane × 4 HCl | Red-violet | +++ |
| 2-Methylamino-3-amino-6-methoxy-pyridine × 2 HCl | Blue-black | +++ |
| 2-(2,5-Diaminophenyl)-ethanol × H$_2$SO$_4$ | Dark violet | +++ |
| 2-Aminomethyl-4-aminophenol × 2HCl | Orange-brown | ++ |
| N,N-bis-(2-hydroxyethyl)-p-phenylene-diamine × HCl | Black-blue | +++ |
| 4,4'-Diaminodiphenylamine × H$_2$SO$_4$ | Black-blue | +++ |
| 2,6-Dimethoxy-3,5-diamino-pyridine × 2 HCl | Dark brown | +++ |
| 3,4-Diaminobenzoic acid | Dark Violet | ++(+) |
| 4-Hydroxy-2,5,6-triaminopyrimidine sulfate | Brown pink | +(+) |

Coloring with the reaction product of components A and B

Component A: 4-formyl-1-methlquinolinium methanesulfonate

Component B: N,N-bis-(2-hydroxyethyl)-p-phenylenediamine×HCl

Shade: black-blue, depth of color +++

TABLE 8

Coloring with 4-(2-formylvinyl)-1-methylquinolinium trifluoromethanesulfonate

| Component B | Shade | Depth of color |
|---|---|---|
| — | Brown-yellow | + |
| 2,5-Diaminotoluene × H$_2$SO$_4$ | Violet-red | ++(+) |
| 2-Methylamino-3-amino-6-methoxy-pyridine × 2 HCl | Red-black | +++ |

TABLE 8-continued

Coloring with 4-(2-formylvinyl)-1-methylquinolinium trifluoromethanesulfonate

| Component B | Shade | Depth of color |
|---|---|---|
| 2-(2,5-Diaminophenyl)-ethanol × H₂SO₄ | Red | ++(+) |
| 2-Aminomethyl-4-aminophenol × 2HCl | Brown-yellow/bronze | ++ |
| 4,4'-Diaminodiphenylamine × H₂SO₄ | Black-violet | +++ |
| 2,6-Dimethoxy-3,5-diamino-pyridine × 2 HCl | Blue-black | +++ |

TABLE 9

Coloring with 4-acetylquinolinium methanesulfonate

| Component B | Shade | Depth of color |
|---|---|---|
| 2,5-Diaminotoluene × H₂SO₄ | Red-brown | ++ |
| 2-(2,5-Diaminophenyl)-ethanol × H₂SO₄ | Red-brown | ++ |
| 2-Aminomethyl-4-aminophenol × 2HCl | Orange-brown | +(+) |
| N,N-bis-(2-hydroxyethyl)-p-phenylene-diamine × HCl | Dark brown | ++(+) |
| 2-Amino-4-(2-hydroxyethylamine)-anisole × H₂SO₄ (Lehmann's blue) | Grey-black | ++(+) |
| 3-Methyl-p-aminophenol | Orange-brown | +(+) |
| 5-Amino-o-cresol | Red-brown | ++ |

TABLE 10

Coloring with 4-pyridinecarboxaldehyde-N-oxide

| Component B | Shade | Depth of color |
|---|---|---|
| 2,4,5,6-Tetraaminopyrimidine × H₂SO₄ | Yelow | ++ |
| 2-Methylamino-3-amino-6-methoxy-pyridine × 2 HCl | Orange-brown | ++ |
| N,N-bis-(2-hydroxyethyl)-p-phenylene-diamine × 2 HCl | Yellow-brown | ++ |

What is claimed is:

1. A method for coloring keratin containing fibers which comprises: applying to the keratin containing fibers a composition comprising:

A) at least one of onium aldehydes and onium ketones of the formula I and derivatives thereof:

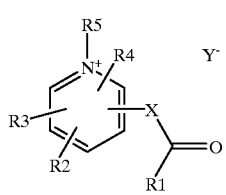

(I)

in which $R^1$ is a hydrogen atom, a $(C_{1-4})$ alkyl group, an aryl group or a heteroaryl group, $R^2$, $R^3$ and $R^4$ independently of one another represent a hydrogen atom, a halogen atom, a $(C_{1-4})$ alkyl group, a $(C_{1-4})$ alkoxy group, hydroxy-$(C_{1-4})$-alkoxy group, hydroxy group, nitro group, aryl group, trifluoromethyl group, amino group which may be substituted by $(C_{1-4})$ alkyl groups or a $(C_{1-4})$ acyl group; two of the substituents together may also form a fused benzene ring, $R^5$ is a $(C_{1-4})$ alkyl group, aryl group, aralkyl group or heteroaryl group, X is a direct bond or a vinylene or phenylene group which may be substituted and Y is halide, benzenesulfonate, p-toluene sulfonate, methane sulfonate, trifluoromethane sulfonate, perchlorate, sulfate, hydrogen sulfate or tetrachlorozincate or the N-oxide of the heterocycle; in combination with B) at least one compound selected from the group consisting of primary aliphatic amines, secondary aliphatic amines, aromatic amines, nitrogen-containing heterocyclic compounds, α- to ω-amino acids, oligopeptides comprising 2 to 9 amino acids, aromatic hydroxy compounds and CH-active compounds; the reaction product of A) with B) can also be present.

2. A composition for coloring keratin-containing fibers comprising:

(A) at least one member selected from the group consisting of onium aldehydes, onium ketones of the formula I and derivatives thereof:

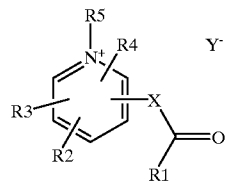

(I)

in which $R^1$ is a hydrogen atom, a $(C_{1-4})$ alkyl group, an aryl group or a heteroaryl group, $R^2$, $R^3$ and $R^4$ independently of one another represent a hydrogen atom, a halogen atom, a $(C_{1-4})$ alkyl group, a $(C_{1-4})$ alkoxy group hydroxy-$(C_{1-4})$-alkoxy group, hydroxy group, nitro group, aryl group, trifluoromethyl group, amino group which may be substituted by $(C_{1-4})$ alkyl groups or a $(C_{1-4})$ acyl group; two of these substituents together may also form a fused benzene ring, $R^5$ is a $(C_{1-4})$ alkyl group, aryl group, aralkyl group or heteroaryl group, X is a direct bond or a vinylene or phenylene group which may be substituted and Y is halide, benzenesulfonate, p-toluene sulfonate, methane sulfonate, trifluoromethane sulfonate, perchlorate, sulfate, hydrogen sulfate or tetrachlorozincate or the N-oxide of the heterocycle; and (B) at least one compound selected from the group consisting of primary aliphatic amines, secondary aliphatic amines, aromatic amines, nitrogen-containing heterocyclic compounds, α- to ω-amino acids, oligopeptides comprising 2 to 9 amino acids, aromatic hydroxy compounds and CH-active compounds;

the reaction product of components A and B may also be present.

3. The composition as claimed in claim 2, wherein component A comprises a member selected from the group consisting of benzenesulfonates, p-toluene sulfonates, methane sulfonates, trifluoromethane sulfonates, perchlorates, sulfates, chlorides, bromides, iodides and/or tetrachlorozincates of 4-formyl-1-methyl pyridinium, 3-formyl-1-methyl pyridinium, 2-formyl-1-methyl pyridinium, 4-formyl-1-ethyl pyridinium, 2-formyl-1-ethyl pyridinium, 4-formyl-1- benzyl pyridinium, 2-formyl-1-benzyl pyridinium, 4-formyl-1,2-dimethyl pyridinium, 4-formyl-1,3-dimethyl pyridinium, 4-formyl-1-methyl quinolinium, 2-formyl-1-methyl quinolinium, 4-(2-formylvinyl)-1-methyl quinolinium, 4-acetyl-1-methyl pyridinium, 2-acetyl-1-methyl pyridinium, 4-acetyl-1-quinolinium, 4-acetyl-1-methyl quinolinium and 4-(2-formylvinyl)-1-methyl pyridinium, 2,6-dichloro-4-formyl-1-methyl pyridinium, 2,6-diphenyl-4-formyl-1-methyl pyridinium, 4-benzoyl-1-methyl pyridinium, 4-propionyl-1-methyl pyridinium, 2-oximomethyl-1-methyl pyridinium, 4-pyridine carboxaldehyde-N-oxide, N-methyl pyridoxal and mixtures thereof.

4. The composition as claimed in claim 2 wherein the compounds of component B comprise at least one member selected from the group consisting of N-(2-hydroxyethyl)-N-ethyl-, N-(2-methoxyethyl)-, 2,3-, 2,4-, 2,5-dichloro-p-phenylenediamine, 2-chloro-p-phenylenediamine, N,N-bis-(2-hydroxyethyl)-p-phenylenediamine, 2,5-dihydroxy-4-morpholinoaniline dihydrobromide, 2-, 3-, 4-aminophenol, o-, p-phenylenediamine, 2,4-diaminophenoxyethanol, 2-(2, 5-diaminophenyl)-ethanol, 2,5-diaminotoluene, -phenol, -phenethol, 4-methylamino-, 3-amino-4-(2'-hydroxyethyloxy)-, 3,4-methylenediamino-, 3,4-methylenedioxyaniline, 3-amino-2,4-dichloro-, 4-methylamino-, 3-amino-4-(2'-hydroxyethyloxy)-, 3,4-methylenediamino-, 3,4-methylenedioxyaniline, 3-amino-2, 4-dichloro-, 4-methylamino-, 3,4-methylenedioxy-, 3-methyl-4-amino-, 2-methyl-5-(2-hydroxyethylamino)-, 6-methyl-3-amino-2-chloro-, 5-(2-hydroxyethylamino)-4-methoxy-2-methyl-, 4-amino-2-aminomethyl phenol, 4-amino-2-hydroxymethyl phenol, 3,4-methylenedioxyphenol, 1,3-diamino-2,4-dimethoxybenzene, 2-, 3-, 4-aminobenzoic acid, -phenylacetic acid, 2,3-, 2,4-, 2,5-, 3,4-, 3,5-diaminobenzoic acid, 4-, 5-aminosalicylic acid, 3-amino-4-hydroxy-, 4-amino-3-hydroxybenzoic acid, 2-, 3-, 4-aminobenzenesulfonic acid, 3amino-4-hydroxybenzenesulfonic acid, 4-amino-3-hydroxynaphthalene sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-, 1,2,4-triaminobenzene, 1,2,4,5-tetraaminobenzene tetrahydrochloride, 2,4,5-triaminophenol trihydrochloride, pentaaminobenzene pentahydrochloride, hexaaminobenzene hexahydrochloride, 2,4,6-triaminoresorcinol trihydrochloride, 4,5-diaminopyrocatechol sulfate, 4,6-diaminopyrogallol dihydrochloride, 3,5-diamino-4-hydroxypyrocatechol sulfate, aromatic anilines and phenols containing another aromatic radical, such as 4,4'-diaminostilbene dihydrochloride, 4,4'-diaminostilbene-2,2'-disulfonic acid sodium salt, 4,4'-diaminodiphenyl methane, -sulfide, -sulfoxide, -amine, 4,4'-diaminodiphenylamine-2-sulfonic acid, 4,4'-diaminobenzophenone, -diphenyl ether, 3,3',4,4'-tetraaminodiphenyl tetrahydrochloride, 3,3'4,4'-tetraaminobenzophenone, 1,3-bis-(2,4-diaminophenoxy)-propane tetrahydrochloride, 1,8-bis-(2,5-diaminophenoxy)-3,6-dioxaoctane tetrahydrochloride, 1,3-bis-(4-aminophenylamino)-propane, -2-propanol, 1,3-bis-[N-(4-aminophenyl)-2-hydroxyethylamino]-2-propanol, N,N-bis-[2-(4-aminophenoxy)-ethyl]-methylamine trihydrochloride, 2-, 3-, 4-amino-, 2-amino-3-hydroxy-, 2,6-diamino-, 2,5-diamino-, 2,3-diamino-, 2-dimethylamino-5-amino-, 3-amino-2-methylamino-6-methoxy-, 2,3-diamino-6-methoxy-, 3,5-diamino-2,6-dimethoxy-, 2,4,5-triamino-, 2,6-dihydroxy-3,4-dimethyl pyridine, 4,5,6-triamino-, 2-hydroxy-4,5,6-triamino-, 4-hydroxy-2,5,6-triamino-, 2,4,5,6-tetraamino-, 2-methylamino-4,5,6-triamino-, 2,4-, 4,5-diamino-, 2-amino-4-methoxy-6-methyl pyrimidine, 2,3,4-trimethyl pyrrole, 2,4-dimethyl-3-ethyl pyrrole, 3, 5-diaminopyrazole, -1,2,4-triazole, 3-amino-, 3-amino-5-hydroxypyrazole, 2-, 3-, 8-aminoquinoline, 4-aminoquinaldine, 2-, 6-aminonicotinic acid, 5-aminoisoquinoline, 5-, 6-aminoindazole, 5-, 7-aminobenzimidazole, -benzothiazole, 2,5-dihydroxy-4-morpholinoaniline and indole and indoline derivatives, such as 4-, 5-, 6-, 7-aminoindole, 4-, 5-, 6-, 7-hydroxyindole, 5,6-dihydroxyindole, 5,6-dihydroxyindoline, 4-hydroxyindoline, physiologically compatible salts of these nitrogen containing heterocyclic compounds formed with inorganic acids, 2-, 4-, 5-methyl resorcinol, 2,5-dimethyl resorcinol, resorcinol, 3-methoxyphenol, pyrocatechol, hydroquinone, pyrogallol, phloroglucinol, hydroxyhydroquinone, 2-, 3-, 4-methoxy-, 3-dimethylamino-, 2-(2-hydroxyethyl)-, 3,4-methylenedioxyphenol, 2,4-, 3,4-dihydroxybenzoic acid, -phenylacetic acid, gallic acid, 2,4,6-trihydroxybenzoic acid, -acetophenone, 2-, 4-chlororesorcinol, 1-naphthol, 1,5-, 2,3-, 2,7-dihydroxynaphthalene, 6-dimethylamino-4-hydroxy-2-naphthalene sulfonic acid, 3,6-dihydroxy-2,7-naphthalene sulfonic acid, 1,2,3,3-tetramethyl-3H-indolium iodide, 1,2,3,3-tetramethyl-3-indolium-p-toluene sulfonate, 1,2,3,3-tetramethyl-3-indolium methane sulfonate, 2,3-dimethylbenzothiazolium iodide, 2,3-dimethylbenzothiazolium-p-toluene sulfonate, rhodanine, rhodanine-3-acetic acid, 1-ethyl(methyl)-2-quinaldinium iodide, barbituric acid, thiobarbituric acid, 1,3-dimethyl (ethyl) thiobarbituric acid, oxindole, coumaranone and 1-methyl-3-phenyl-2-pyrazolinone.

5. The composition as claimed in claim 2, wherein the compounds of components A and B are each present in a quantity of 0.03 to 65 mmol, based on 100 g of the colorant as a whole.

6. The composition as claimed in claim 7, comprising oxidizing agents in a quantity of 0.01 to 6% by weight, based on the solution applied.

7. The composition as claimed in claim 2, wherein $H_2O_2$ comprises the oxidizing agent.

8. The composition as claimed in claim 2, comprising a surfactant selected from the group consisting of anionic surfactants, zwitterionic surfactants, nonionic surfactants and mixtures thereof.

9. The process for coloring keratin-containing fibers of claim 1, wherein the composition further comprising typical cosmetic ingredients is applied to the keratin-containing fibers, left thereon for about 30 minutes, and then rinsed out or washed out with a shampoo.

10. The method of claim 1, wherein the composition applied to the keratin containing fibers further comprises from 0.01% to 6% by weight of an oxidizing agent based on the contacting composition.

11. The method of claim 10 wherein the oxidizing agent comprises $H_2O_2$.

12. The composition of claim 5 wherein the composition further comprises from 0.01 to 6% by weight of oxidizing agents based on the weight of a composition for application to keratin containing fibers.

13. The composition of claim 12, wherein the oxidizing agent comprises $H_2O_2$.

14. The composition of claim 13, further comprising a surfactant selected from the group consisting of anionic surfactants, zwitterionic surfactants, nonionic surfactants and mixtures thereof.

15. The composition of claim 3, wherein the compounds of components A and B are each present in a quantity of 0.03 to 65 mmol, based on 100 g of the colorant as a whole.

16. The composition of claim 15, comprising oxidizing agents in a quantity of 0.01 to 6% by weight, based on the solution applied.

17. The composition of claim 16, wherein $H_2O_2$ comprises the oxidizing agent.

18. The composition of claim 17, comprising a surfactant selected from the group consisting of anionic surfactants, zwitterionic surfactants, nonionic surfactants and mixtures thereof.

19. The composition of claim 3, wherein the compounds of component B comprise at least one member selected from the group consisting of N-(2-hydroxyethyl)-N-ethyl-, N-(2-methoxyethyl)-, 2,3-, 2,4-, 2,5-dichloro-p-phenylenediamine, 2-chloro-p-phenylenediamine, N,N-bis-(2-hydroxyethyl)-p-phenylenediamine, 2,5-dihydroxy-4-morpholinoaniline dihydrobromide, 2-, 3-, 4-aminophenol, o-, p-phenylenediamine, 2,4-diaminophenoxyethanol, 2-(2,5-diaminophenyl)-ethanol, 2,5-diaminotoluene, -phenol, -phenethol, 4-methylamino-, 3-amino-4-(2'-hydroxyethyloxy)-, 3,4-methylenediamino-, 3,4-methylenedioxyaniline, 3-amino-2,4-dichloro-, 4-methylamino-, 3-amino-4-(2'-hydroxyethyloxy)-, 3,4-methylenediamino-, 3,4-methylenedioxyaniline, 3-amino-2,4-dichloro-, 4-methylamino-, 3,4-methylenedioxy-, 3-methyl4-amino-, 2-methyl-5-(2-hydroxyethylamino)-, 6-methyl-3-amino-2-chloro-, 5-(2-hydroxyethylamino)-4-methoxy-2-methyl-, 4-amino-2-aminomethyl phenol, 4-amino-2-hydroxymethyl phenol, 3,4-methylenedioxyphenol, 1,3-diamino-2,4-dimethoxybenzene, 2-, 3-, 4-aminobenzoic acid, -phenylacetic acid, 2,3-, 2,4-, 2,5-, 3,4-, 3,5-diaminobenzoic acid, 4-, 5-aminosalicylic acid, 3-amino-4-hydroxy-, 4-amino-3-hydroxybenzoic acid, 2-, 3-, 4-aminobenzenesulfonic acid, 3-amino-4-hydroxybenzenesulfonic acid, 4-amino-3-hydroxynaphthalene sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-, 1,2,4-triaminobenzene, 1,2,4,5-tetraaminobenzene tetrahydrochloride, 2,4,5-triaminophenol trihydrochloride, pentaaminobenzene pentahydrochloride, hexaaminobenzene hexahydrochloride, 2,4,6-triaminoresorcinol trihydrochloride, 4,5-diaminopyrocatechol sulfate, 4,6-diaminopyrogallol dihydrochloride, 3,5-diamino-4-hydroxypyrocatechol sulfate, aromatic anilines and phenols containing another aromatic radical, such as 4,4'-diaminostilbene dihydrochloride, 4,4'-diaminostilbene-2,2'-disulfonic acid sodium salt, 4,4'-diaminodiphenyl methane, -sulfide, -sulfoxide, -amine, 4,4'-diaminodiphenylamine-2-sulfonic acid, 4,4'-diaminobenzophenone, -diphenyl ether, 3,3',4,4'-tetraaminodiphenyl tetrahydrochloride, 3,3'4,4'-tetraaminobenzophenone, 1,3-bis-(2,4-diaminophenoxy)-propane tetrahydrochloride, 1,8-bis-(2,5-diaminophenoxy)-3,6-dioxaoctane tetrahydrochloride, 1,3-bis-(4-aminophenylamino)-propane, -2-propanol, 1,3-bis-[N-(4-aminophenyl)-2-hydroxyethylamino]-2-propanol, N,N-bis-[2-(4-aminophenoxy)-ethyl]-methylamine trihydrochloride, 2-, 3-, 4-amino-, 2-amino-3-hydroxy-, 2,6-diamino-, 2,5-diamino-, 2,3-diamino-, 2-dimethylamino-5-amino-, 3-amino-2-methylamino-6-methoxy-, 2,3-diamino-6-methoxy-, 3,5-diamino-2,6-dimethoxy-, 2,4,5-triamino-, 2,6-dihydroxy-3,4-dimethyl pyridine, 4,5,6-triamino-, 2-hydroxy-4,5,6-triamino-, 4-hydroxy-2,5,6-triamino-, 2,4,5,6-tetraamino-, 2-methylamino-4,5,6-triamino-, 2,4-, 4,5-diamino-, 2-amino4-methoxy-6-methyl pyrimidine, 2,3,4-trimethyl pyrrole, 2,4-dimethyl-3-ethyl pyrrole, 3,5-diaminopyrazole, -1,2,4-triazole, 3-amino-, 3-amino-5-hydroxypyrazole, 2-, 3-, 8-aminoquinoline, 4-aminoquinaldine, 2-, 6-aminonicotinic acid, 5-aminoisoquinoline, 5-, 6-aminoindazole, 5-, 7-aminobenzimidazole, -benzothiazole, 2,5-dihydroxy4-morpholinoaniline and indole and indoline derivatives, such as 4-, 5-, 6-, 7-aminoindole, 4-, 5-, 6-, 7-hydroxyindole, 5,6-dihydroxyindole, 5,6-dihydroxyindoline, 4-hydroxyindoline, physiologically compatible salts of these nitrogen containing heterocyclic compounds formed with inorganic acids, 2-, 4-, 5-methyl resorcinol, 2,5-dimethyl resorcinol, resorcinol, 3-methoxyphenol, pyrocatechol, hydroquinone, pyrogallol, phloroglucinol, hydroxyhydroquinone, 2-, 3-, 4-methoxy-, 3-dimethylamino-, 2-(2-hydroxyethyl)-, 3,4-methylenedioxyphenol, 2,4-, 3,4-dihydroxybenzoic acid, -phenylacetic acid, gallic acid, 2,4,6-trihydroxybenzoic acid, -acetophenone, 2-, 4-chlororesorcinol, 1-naphthol, 1,5-, 2,3-, 2,7-dihydroxynaphthalene, 6-dimethylamino-4-hydroxy-2-naphthalene sulfonic acid, 3,6-dihydroxy-2,7-naphthalene sulfonic acid, 1,2,3,3-tetramethyl-3H-indolium iodide, 1,2,3,3-tetramethyl-3-indolium-p-toluene sulfonate, 1,2,3,3-tetramethyl-3-indolium methane sulfonate, 2,3-dimethylbenzothiazolium iodide, 2,3-dimethylbenzothiazolium-p-toluene sulfonate, rhodanine, rhodanine-3-acetic acid, 1-ethyl(methyl)-2-quinaldinium iodide, barbituric acid, thiobarbituric acid, 1,3-dimethyl (ethyl) thiobarbituric acid, oxindole, coumaranone and 1-methyl-3-phenyl-2-pyrazolinone.

20. The composition of claim 19, wherein the compounds of components A and B are each present in a quantity of 0.03 to 65 mmol, based on 100 g of the colorant as a whole.

21. The composition of claim 20, comprising oxidizing agents in a quantity of 0.01 to 6% by weight, based on the solution applied.

22. The composition of claim 21, wherein $H_2O_2$ comprises the oxidizing agent.

23. The composition of claim 22, comprising a surfactant selected from the group consisting of anionic surfactants, zwitterionic surfactants, nonionic surfactants and mixtures thereof.

* * * * *

UNITED STATES PATENT AND TRADEMARK OFFICE
CERTIFICATE OF CORRECTION

PATENT NO. : 6,371,993 B1  Page 1 of 1
DATED : April 16, 2002
INVENTOR(S) : Moeller et al.

It is certified that error appears in the above-identified patent and that said Letters Patent is hereby corrected as shown below:

<u>Title page, Item [54] and Column 1, line 2,</u>
Delete "DYING" and insert therefor -- DYEING --.
Item [56], FOREIGN PATENT DOCUMENTS,
Delete "38 23 354", and insert therefor -- 37 23 354--.

<u>Column 17,</u>
Line 38, delete "3amino-4-", and insert therefor -- 3-amino-4- --.

<u>Column 18,</u>
Line 40, delete "claim 7", and insert therefor -- claim 2 --.

<u>Column 19,</u>
Line 30, delete "3-methy14-amino-", and insert therefor -- 3-methyl-4-amino- --.

<u>Column 20,</u>
Line 14, delete "2-amino4-methoxy-6-methyl", and insert therefor
-- 2-amino-4-methoxy-6-methyl --.
Line 20, delete "2,5-dihydroxy4-", and insert therefor -- 2,5-dihydroxy-4- --.

Signed and Sealed this

Nineteenth Day of August, 2003

JAMES E. ROGAN
*Director of the United States Patent and Trademark Office*